United States Patent [19]

Crosby et al.

[11] 4,288,387

[45] Sep. 8, 1981

[54] PROCESS FOR THE PREPARATION OF CYCLOPROPANE CARBOXYLIC ACID ESTERS

[75] Inventors: John Crosby, Cheshire; David Holland, Cheshire; Dale A. Laidler, Cheshire; David J. Milner, Manchester, all of England

[73] Assignee: Imperial Chemical Industries Limited, London, England

[21] Appl. No.: 156,077

[22] Filed: Jun. 2, 1980

[30] Foreign Application Priority Data

Jul. 13, 1979 [GB] United Kingdom ............... 24521/79

[51] Int. Cl.$^3$ ..................... C07C 69/74; C07C 121/75
[52] U.S. Cl. .................................. 260/465 D; 260/124
[58] Field of Search ..................... 260/465 D; 560/124

[56] References Cited

U.S. PATENT DOCUMENTS

| | | | |
|---|---|---|---|
| 3,868,401 | 2/1975 | Aratani et al. | 560/124 |
| 4,029,690 | 1/1977 | Aratani et al. | 560/124 |
| 4,166,064 | 8/1979 | Kondo et al. | 560/124 X |
| 4,183,948 | 1/1980 | Huff | 260/465 D X |

FOREIGN PATENT DOCUMENTS

| | | |
|---|---|---|
| 863151 | 7/1978 | Belgium . |
| 50-160241 | 12/1975 | Japan . |
| 740014 | 11/1955 | United Kingdom . |
| 1455189 | 11/1976 | United Kingdom . |

*Primary Examiner*—Dolph H. Torrence
*Attorney, Agent, or Firm*—Cushman, Darby & Cushman

[57] ABSTRACT

3-Halogenoethyl- or propyl-2,2-dimethylcyclopropane carboxylic acid esters, which are intermediates in the preparation of synthetic pyrethroids, are prepared by the reaction of certain halogenopentenes or hexenes with a diazoacetic ester in the presence of a catalyst which is metallic copper or a copper (II) salt, a rhodium (II) salt of a carboxylic acid or a transition metal complex of certain chiral Schiff bases. By the use of the latter class of catalysts the yield of preferred cis IR isomer may be increased relative to the other possible isomers.

10 Claims, No Drawings

PROCESS FOR THE PREPARATION OF CYCLOPROPANE CARBOXYLIC ACID ESTERS

This invention relates to a process for the preparation of 3-halogeno-ethyl- or propyl-2,2-dimethylcyclopropane-1-carboxylic acid esters which are precursors of synthetic pyrethroid insecticides.

It is known from United Kingdom Patent Specification No. 740,014 to react an alkyl diazoacetate with 2,5-dimethylhexa-2,4-diene in the presence of a copper catalyst to give an alkyl ester of chrysanthemic acid.

Also, United Kingdom Patent Specification No. 1455189 discloses the asymmetric synthesis of alkyl chrysanthemates by reacting 2,5-dimethylhexa-2,4-diene with an alkyl diazoacetate in the presence of catalysts which are copper complexes of certain chiral Schiff bases.

Belgian Patent Specification No. 863151 discloses the preparation of compounds of the formula:

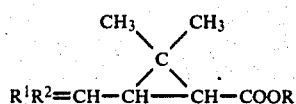

wherein R is a lower alkyl group and $R^1$ and $R^2$ are such that, inter alia, one of $R^1$ and $R^2$ represents a trifluoromethyl group and the other represents a halogen atom, by reacting a diene of formula $R^1R^2=CH-CH=C(CH_3)_2$ with a lower alkyl ester of diazoacetic acid. This reaction is conveniently conducted using an excess of the diene as a solvent for the alkyl diazoacetate in the presence of a metallic catalyst, for example, powdered copper or copper bronze.

It has now been found that this reaction can be extended to halogenated monoenes to give compounds which are useful as precursors of pyrethroid insecticides.

According to the present invention there is provided a process for the preparation of a compound of the formula:

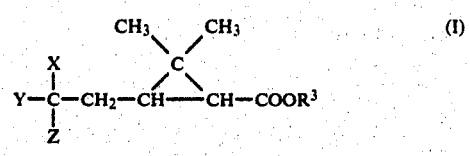

wherein
$R^3$ is an alkyl, 3-phenoxybenzyl, α-cyano-3-phenoxybenzyl or α-ethynyl-3-phenoxybenzyl group,
Z is fluorine, chlorine or bromine, and
X and Y, which may be the same or different, are fluorine, chlorine, bromine, lower alkyl or $Q(CF_2)_m-$, in which Q is hydrogen, fluorine or chlorine and m is 1 or 2, or

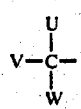

in which each of U, V and W are independently hydrogen, fluorine or chlorine except that where one of X and Y is a group of formula $Q(CF_2)_m-$ where Q is as defined above, the other of X and Y is fluorine, chlorine or bromine or a group

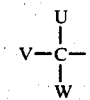

as previously defined,
which comprises reacting a compound having the formula:

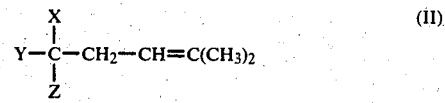

with an alkyl diazoacetate $N_2CH.COOR^3$, $R^3$, X, Y and Z having the previously defined meanings, in the presence of a catalyst selected from the following classes (i) to (vi):
  (i) metallic copper, or a copper(II) salt,
  (ii) rhodium(II) salts of carboxylic acids,
  (iii) the copper complex of a chiral Schiff base having the formula:

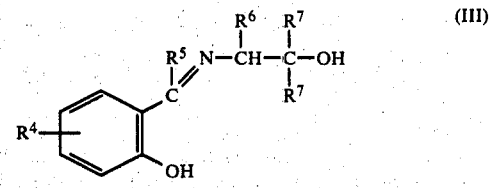

in which
$R^4$ is hydrogen, alkyl, aralkyl, aryl or a substituent containing a hetero atom, or $R^4$, when taken with the aromatic nucleus to which it is attached, forms a naphthalene ring system,
$R^5$ is hydrogen, alkyl, aralkyl or aryl
and $R^6$ and $R^7$ are each alkyl, aralkyl or aryl,
  (iv) the transition metal complex of a chiral Schiff base having the general formula:

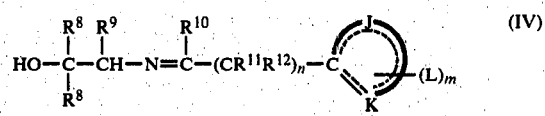

wherein
$R^8$ and $R^9$, which may be the same or different, are alkyl, aralkyl or aryl;
$R^{10}$ is hydrogen or lower alkyl, aryl, aralkyl or alkaryl,
$R^{11}$ and $R^{12}$, which may be the same or different are hydrogen or lower alkyl, or where n is 1, may with the cyclic system to which $CR^{11}R^{12}$ is attached, form a fused ring system,
J is a chain of 3 or 4 atoms consisting either exclusively of carbon atoms or of carbon atoms together with one or more hetero-atoms which may be the same or different, which chain with the group —C—K— forms an aromatic system,
K is nitrogen, N→O or —NH—,
L, each of which may be the same or different, represents a substituent attached to a carbon atom in the chain J and is hydrogen, alkyl, aralkyl, aryl or a substituent containing a hetero-atom, or two groups L together with the ring to which they are attached, form a fused ring system, n is 0, 1 or 2, and m is the number of carbon atoms in the chain J, (v) the transition metal complex of a chiral Schiff base having the general formula:

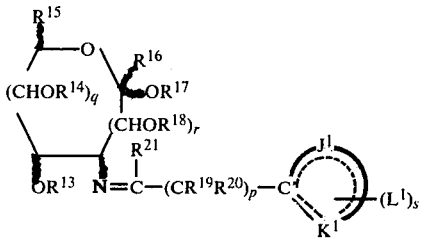

(V)

wherein $R^{13}$, $R^{14}$, and $R^{18}$, which may be the same or different, are hydrogen or lower alkyl, except that at least one of $R^{13}$ and $R^{18}$ is hydrogen, $R^{15}$ is hydrogen, a sugar derivative or —$CH_2OR^{22}$ in which $R^{22}$ is hydrogen, lower alkyl or together with $R^{14}$ forms a divalent hydrocarbon group, $R^{16}$ is hydrogen or —$CH_2OH$, $R^{17}$ is hydrogen, lower alkyl or a sugar derivative, $R^{19}$ and $R^{20}$, which may be the same or different, are hydrogen or lower alkyl, or where p is 1, may with the cyclic system to which $CR^{19}R^{20}$ is attached form a fused ring system, $R^{21}$ is hydrogen, alkyl, aralkyl or aryl, $J^1$ is a chain of 3 or 4 atoms consisting either exclusively of carbon atoms or of carbon atoms together with one or more hetero atoms which may be the same or different, which chain with the group —C≐K— forms an aromatic system, K is C—OH, nitrogen, N→O or —NH—, $L^1$, each of which may be the same or different, represents a substituent attached to a carbon atom in the chain $J^1$ and is hydrogen, alkyl, aralkyl, aryl or a substituent containing a hetero-atom, or two groups $L^1$ together with the ring to which they are attached form a fused ring system, r is 0 or 1, q is 0, 1 or 2, provided that q+r is 1, 2 or 3, p is 0, 1 or 2, and s is the number of carbon atoms in the chain $J^1$, and (vi) the transition metal complex of a chiral Schiff base having the general formula:

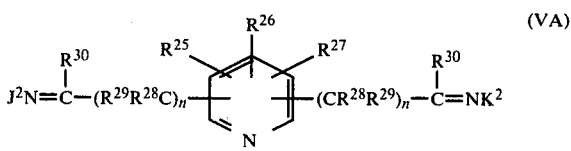

(VA)

wherein $R^{25}$, $R^{26}$ and $R^{27}$, which may be the same or different, are hydrogen, alkyl, aralkyl, aryl, a substituent containing a hetero atom, or two of $R^{25}$, $R^{26}$ and $R^{27}$ together with the pyridine ring from a fused ring system, $R^{28}$ and $R^{29}$, which may be the same or different, are hydrogen, lower alkyl, or, where n is 1, may with the pyridine ring to which $CR^{28}R^{29}$ is attached, form a fused ring system, $R^{30}$ is hydrogen, alkyl, aralkyl or aryl, n is 0, 1 or 2 and $J^2$ and $K^2$, which may be the same or different, are groups of the formulae:

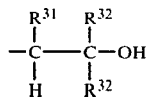

(VB)

or

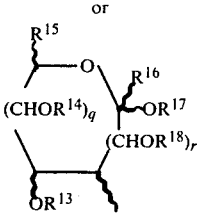

(VC)

in which $R^{31}$ and $R^{32}$, which may be the same or different, are alkyl, aralkyl or aryl, and $R^{13}$, $R^{14}$, $R^{15}$, $R^{16}$, $R^{17}$, $R^{18}$, q and r have the previously defined meanings, and the corresponding compounds having an oxygen atom attached to the pyridine ring nitrogen.

In the above definition the term "lower alkyl" means an alkyl group containing up to 5 carbon atoms.

The process according to the present invention is preferably carried out in the presence of an inert solvent in which the cyclopropane product of formula (I) is soluble.

Conveniently the solvent used is immiscible with water to facilitate preparation of the diazoacetic ester. More preferably the solvent also has a boiling point lower than that of the monoene of formula (II) to facilitate recovery of unreacted monoene.

Suitable solvents include saturated chlorinated hydrocarbon solvents, such as ethylene dichloride, dichloromethane, tetrachloroethane and carbon tetrachloride, and hydrocarbon solvents such as toluene.

The concentration of catalyst in the reaction mixture is not critical, but generally concentrations equivalent to 0.00001 to 1 g atoms of transition metal per liter of reaction mixture, and especially 0.005 to 1 g atoms, are suitable. The temperature of reaction is generally in the range 0° to 130° C., preferably 10° C. to 90° C.

The diazoacetic acid ester may be prepared by reacting a water soluble acid addition salt (e.g. the hydrochloride) of an ester of glycine with an alkali metal nitrite in an aqueous medium, which is stirred with a water-immiscible solvent into which the diazoacetic acid ester is extracted. Alkali metal nitrites which may be used are, for example, the potassium or sodium salts, and the reaction with the glycine ester is preferably carried out in the presence of an acid catalyst, for example, sulphuric acid.

The solution of diazoacetic acid ester thus formed is then added to a solution of the monoene of formula (II) maintained at the desired temperature, and containing the catalyst, usually in solution.

It is usual to use excess monoene, the ratio of monoene to diazoacetic ester being in the range 1:2 to 10:1.

Progress of the reaction may be monitored by measuring nitrogen evolution, which may also be used to determine yield of total products, the proportion of the desired product being readily determined by gas liquid chromatography (g.l.c.).

Separation of the desired product from the reaction mixture may be achieved by any convenient means; but it is generally convenient to first distil off the solvent, the monoene, then any esters of maleic and fumaric acids and finally the required product. Alternatively, the crude product, where it is a lower alkyl ester, after removal of solvent and unreacted monoene may be used as an intermediate without further purification.

The reaction may also be performed continuously by forming the diazoacetic ester in a first vessel and continuously transferring it, in a solvent, to a second vessel where it is reacted immediately with the monoene.

A starting material of formula (II) in which X is trifluoromethyl and Y and Z are each chlorine may be obtained by heating 5-methyl-2,2,4-trichloro-1,1,1-trifluorohexane in a polar aprotic solvent, for example, dimethylformamide, preferably in the presence of an alkali metal halide, for example, lithium chloride at ca. 130° C. for 9 hours. The desired compound, in admixture with unreacted starting material and 2-chloro-5-methyl-1,1,1-trifluorohexa-2,4-diene, is isolated from the reaction mixture by drowning the reaction mixture into water to precipitate most of the product, recovering the remainder by extraction of the aqueous liquors with methylene chloride and removal of the methylene chloride by distillation, combining the crude products and washing with water to remove dimethylformamide. The product may then be obtained in a pure state by preparative gas-liquid chromatography. This process is more fully described in our copending United Kingdom Patent Application of earlier date.

The starting material of formula (II) in which X, Y and Z are each chlorine may be obtained by heating 3-bromo-1,1,1-trichloro-4-methylpentane in a polar aprotic solvent, for example, dimethylformamide, with an alkali metal halide, for example, lithium bromide at ca. 80° C. for 5 hours. The product may be isolated from the reaction mixture, for example, by dilution with a solvent which is miscible with the reaction mixture but immiscible with water, for example, methylene chloride, followed by washing of the organic layer with water, drying and fractional distillation. This process is more fully described in a co-pending United Kingdom Patent Application.

A compound of formula (I) in which Z is chlorine or bromine may be dehydrohalogenated to give a compound of the formula:

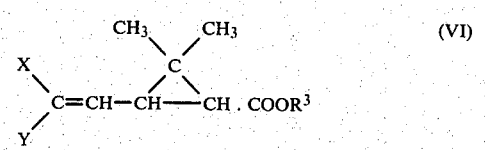

(VI)

in which $R^3$, X and Y have the previously defined meanings. This dehydrohalogenation step may be carried out by reacting the compound of formula (I) with an alkali metal carbonate in a polar aprotic solvent, a process which is more fully described in a co-pending United Kingdom Patent Application.

Compounds of formula (VI) in which $R^3$ is 3-phenoxybenzyl, α-cyano-3-phenoxybenzyl or α-cyano-3-phenoxybenzyl, i.e. compounds having the formula:

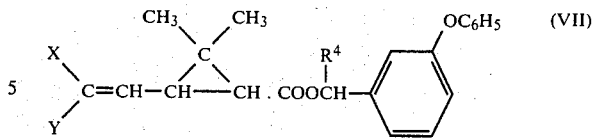

in which $R^4$ is H, CN or —C≡CH, are, in certain isomeric configurations, powerful insecticides, as disclosed in, for example, Belgian Patent Specification No. 863151 already referred to.

Compounds having the above formula (VI) in which $R^3$ is lower alkyl may be converted by conventional methods of organic chemistry into the corresponding insecticidal 3-phenoxybenzyl, α-cyano-3-phenoxybenzyl or α-ethynyl-3-phenoxybenzyl esters. Thus, the compound of formula (VI) in which $R^3$ is lower alkyl may be reacted with m-phenoxybenzyl alcohol or its α-cyano or α-ethynyl derivative in the presence of a transesterification catalyst such as sodium methoxide or ethoxide, or a titanium catalyst such as tetramethyl or tetraethyl titanate, to give the compound of formula (VI) in which $R^3$ is 3-phenoxybenzyl, α-cyano-3-phenoxybenzyl or α-ethynyl-3-phenoxybenzyl. Alternatively, the compound of formula (VI) in which $R^3$ is a lower alkyl group may be hydrolysed to give the corresponding free carboxylic acid [(VI), $R^3$=H], which may then be converted into the acid chloride which is subsequently reacted with m-phenoxybenzyl alcohol or a derivative thereof.

The insecticidal compounds of formula (VII) are capable of existing in various geometrical and stereoisomeric forms. Thus, there are cis and trans isomers arising from the substitution pattern of the cyclopropane ring, and in particular the carbon atom at the 1-position bearing the carboxylic acid ester group may have either the R or S configuration. Consequently when $R^4$=H there are four isomeric possibilities for a compound of formula (VII) arising from the cyclopropane ring substitution, and these may be identified as cis-IR, trans-IR, cis-IS and trans-IS. In terms of insecticidal activity, the compounds having the cis-IR configuration are particularly potent and have substantially higher activity than the compounds having the trans-IR configuration. The corresponding compounds having the IS configuration are essentially insecticidally inactive. By cis we mean that the hydrogen atoms at carbon atoms 1 and 3 of the cyclopropane ring are in cis relationship to one another, and by trans we mean that the said hydrogen atoms are in trans relationship to one another.

In order to achieve the highest level of insecticidal activity it is desirable that compounds of formula (VII) should have the maximum possible content of IR isomers and especially of the cis-IR isomer. The conversion of compounds of formula (I) into compounds of formula (VII) may be carried out without substantial alteration in the proportions of the various isomers, and consequently it is also desirable to obtain compounds of formula (I) having the maximum possible content of IR isomer.

Throughout this specification the term "aromatic system" means an essentially planar cyclic conjugated system containing $(4z+2)\pi$-electrons, z being a positive integer.

It is found that the process of the present invention provides compounds of formula (I) which are rich in the preferred cis-IR isomer. This is an unexpected result because the cis-isomers are considered to be thermodynamically less stable than the trans isomers. Consequently the derived insecticides of formula (VII) will also be rich in cis-IR isomer and have high activity. Furthermore the yield of compound of formula (I) prepared according to the process of the present invention is in general higher than the corresponding yield under similar conditions from a diene of formula $R^1R^2C=CH—CH=C(CH_3)_2$ and a lower alkyl ester of diazoacetic acid as described in Belgian Patent Specification No. 863151 already referred to.

The preferred isomers of compounds of formula (I) are obtained according to the process of the present invention even with such a simple catalyst as copper bronze. Formation of the cis-IR isomer is often further favoured by the use of chiral metal complex catalysts of classes (iii) to (vi) as hereinbefore defined, and, surprisingly this is particularly so when the chiral catalysts have the S configuration, which is generally the configuration of naturally occurring amino-acids and monosaccharides, thus making such catalysts readily accessible.

When the catalyst used in the above-defined process is metallic copper, it may be in the form of, for example, copper powder or copper bronze. Examples of copper-(II) salts which may be used are copper(II) acetate, copper(II) sulphate and copper(II) naphthanate.

An example of rhodium(II) salt of a carboxylic acid which may be used as a catalyst in the process is rhodium(II) pivalate.

Catalysts of the class identified as (iii) above and their preparation are more fully described in United Kingdom Patent Specification No. 1455189 and Japanese Patent Kokai No. 160241/75. Briefly, they may be obtained by, for example, reaction of a chiral amino alcohol having the formula:

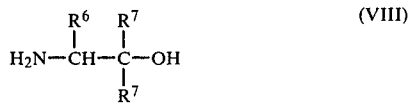

with the bis(salicylaldehydato)copper derivative of a salicylaldehyde compound having the formula:

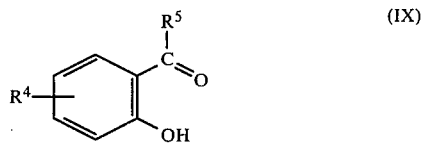

in which $R^4$, $R^5$, $R^6$ and $R^7$ have the previously defined meanings.

With regard to the catalysts of class (iv) derived from a chiral Schiff base having the general formula (IV), specific examples of the chain J are

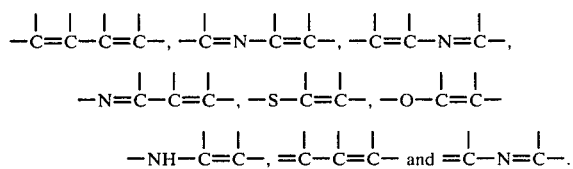

Examples of substituents $R^8$ and $R^9$ in general formula (IV) are methyl, ethyl, n-propyl, isopropyl, n-butyl, isobutyl, sec-butyl, tert-butyl, octyl, cyclohexyl, cyclohexylmethyl, benzyl, benzhydryl, 2,2-diphenylethyl, phenyl, tolyl and naphthyl.

Specific examples of L when it represents a substituent containing at least one hetero atom are OH, $OR^{23}$, $OCOR^{23}$, CHO, $COR^{23}$, $CO_2H$, $CO_2R^{23}$, CN, $CONH_2$, $NH_2$, $NHR^{23}$, $NR^{23}_2$, $NHCOR^{23}$, $NO_2$, SH, $SR^{23}$, $SOR^{23}$, $SO_3R^{23}$, $SO_3H$ or a halogen atom. $R^{23}$ in the above substituents is alkyl, aralkyl or aryl.

Preferred chiral Schiff bases of formula (IV) are those in which $R^8$ is a substituted phenyl group, $R^{10}$ is hydrogen, J is

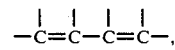

K is nitrogen, L is hydrogen, m is 4 and n is 0 (i.e. the cyclic nucleus in general formula (IV) is a pyridine nucleus). It is also preferred that $R^8$ represents a phenyl group having a substituent at the 2-position or having substituents at the 2,5- or 2,6-positions.

Examples of the substituted phenyl groups represented by $R^8$ are 2-methoxyphenyl, 2-ethoxyphenyl, 2-propoxyphenyl, 2-isopropoxyphenyl, 2-butoxyphenyl, 2-tert-butoxyphenyl, 2-octyloxyphenyl, 2-benzyloxyphenyl, 2-phenoxyphenyl, 2-methoxy-5-methylphenyl, 2-butoxy-5-methylphenyl, 2-benzyloxy-5-methylphenyl, 5-tert-butyl-2-methoxyphenyl, 2-butoxy-5-tert-butylphenyl, 5-tert-butyl-2-octyloxyphenyl, 2-benzyloxy-5-tert-butylphenyl, 4-methoxybiphenyl-3-yl, 2,5-dimethoxyphenyl, 2,5-dibutoxyphenyl, 2,5-dioctyloxyphenyl and 2,5-dibenzyloxyphenyl.

The novel chiral Schiff bases, the metal complexes of which form the catalysts of class (iv) above, may be obtained by reacting a chiral amino alcohol having the formula:

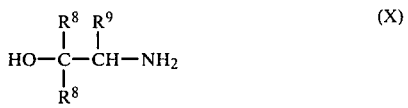

with a carbonyl compound having the formula:

wherein $R^8$, $R^9$, $R^{10}$, $R^{11}$, $R^{12}$, J, K, L, m and n have the previously defined meanings.

The reaction is preferably carried out in the presence of an inert solvent in which the Schiff base is insoluble and is effected near the reflux temperature of the solvent.

Suitable solvents include aromatic hydrocarbons, e.g. toluene, alcohols, e.g. methanol, and halogenated hydrocarbons, e.g. 1,2-dichloroethane and chloroform.

Examples of specific compounds of formula (XII) which may be used to prepare the novel Schiff bases are pyridine-2-carboxaldehyde, 2-acetylpyridine, pyridoxal, quinoline-8-carboxaldehyde, 8-acetylquinoline, pyridine-2-carboxaldehyde-N-oxide and pyrrole-2-carboxaldehyde.

Whilst the chiral amino alcohol of formula (X) may be obtained by optical resolution of a mixture of enantiomers, preferably it is prepared from a chiral starting material. α-Aminoacid esters are convenient starting materials and they may be converted into suitable chiral aminoalcohols by known methods using appropriate Grignard reagents.

An example of an amino-alcohol of formula (X) is 2-amino-1,1-di(2-methoxyphenyl)-3-phenylpropan-1-ol.

The compounds of formula (IV) in which K is N→O may be obtained by oxidation of the corresponding compounds in which K is unsubstituted nitrogen. A suitable oxidising agent for this purpose is hydrogen peroxide.

The catalysts of Class (iv) in which a transition metal is coordinated with a chiral Schiff base have the general formulae:

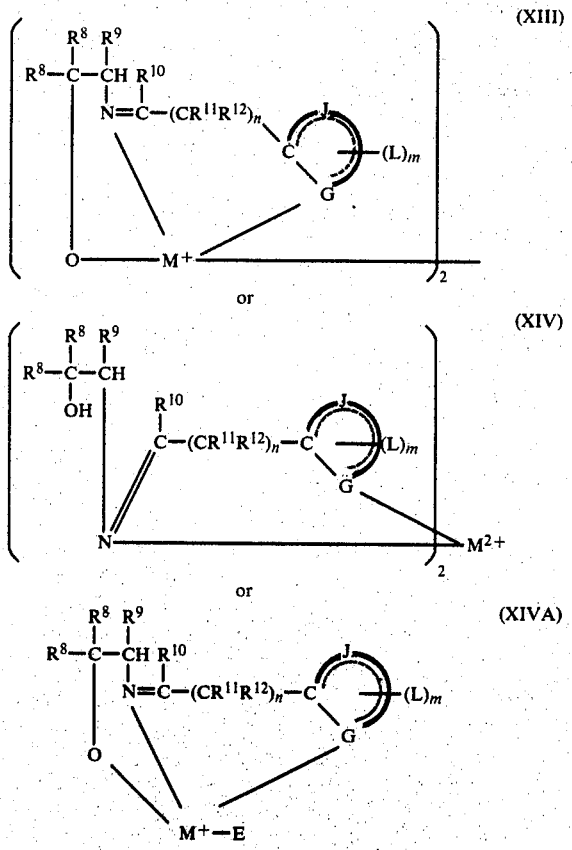

in which $R^8$, $R^9$, $R^{10}$, $R^{11}$, $R^{12}$, J, L, m and n have the previously defined meanings, E is a monodentate netural ligand, M is a metal from the first or second series of the main group of transition metals and G is =N-,

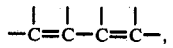

O or —N—.

By transition metal we mean a metal which, in any one of its commonly occurring oxidation states, has only a partly filled d shell. In the first transition metal series the partly filled d shell is 3d. In the second series the partly filled d shell is 4d.

Preferably the metal is copper(II), chromium(II), nickel(II), manganese(II), iron(II), iron(III), cobalt(II) or palladium(II). Particularly preferably the metal is copper(II).

Examples of ligand E in general formula (XIVA) include Lewis bases, such as amines, e.g. pyridine, and tertiary phosphine oxides.

It will be appreciated that complexes according to the general formula (XIII) above are bi-nuclear and complexes according to the general formulae (XIV) and (XIVA) are mono-nuclear, and that in the complexes according to the general formulae (XIII) and (XIVA) the Schiff base behaves as a tridentate ligand and that in complexes according to the general formula (XIV) the Schiff base behaves as a bidentate ligand.

A preferred group of metal complexes for use as catalysts according to the present invention are those of general formula (XIV) since these give a higher optical yield than that given by the metal complexes of general formulae (XIII) or (XIVA).

In the catalysts of general formulae (XIII), (XIV) or (XIVA) it is preferred that $R^8$ is a substituted phenyl group, $R^{10}$ is hydrogen, J is $$-\overset{|}{C}=\overset{|}{C}-\overset{|}{C}=\overset{|}{C}-,$$

G is nitrogen, L is hydrogen and n is 0.

It will be appreciated that in chiral metal complexes as defined in formulae (XIII), (XIV) and (XIVA) where G is =N— or

the metal carries a positive charge and that an anion is necessary to provide an ionically netural compound. The anions associated with the metal complexes may be inorganic or organic, provided that they are derived from strong acids having a pKa value less than 2.5.

The anions should not be oxidising or reducing agents or otherwise chemically reactive with diazoacetic esters or other materials used in the process according to the present invention. Suitable anions include, inter alia, halide, tetrafluoroborate, methosulphate, sulphate, bisulphate, aromatic sulphonate, fluorosilicate and tetraphenylborate.

Various methods are available for preparing the metal complexes of chiral Schiff bases as hereinbefore defined. The Schiff base may be reacted with a suitalbe salt of the appropriate metal. The aminoalcohol may be reacted with an appropriate metal ketone or aldehyde complex, e.g. bis(salicylaldehydato)copper(II). The preferred method involves reacting the Schiff base with an appropriate metal ketone or aldehyde complex; the metal complexes obtained by this method tend to be more selective than those obtained by other methods.

Catalysts of class (iv) and their preparation are the subject of a co-pending United Kingdom Patent Application.

With regard to the catalysts of class (v) derived from a chiral Schiff base having the general formula (V), Specific examples of the conjugated chain $J^1$ are

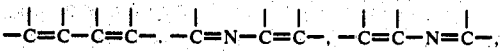

-continued

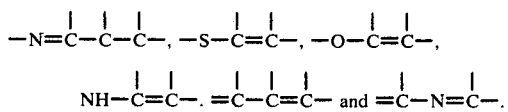

Specific examples of the substituent $L^1$ containing (a) heteroatom(s) are OH, $OR^{24}$, $-CO_2H$, $CO_2R^{24}$, CN, $CONH_2$, $NH_2$, $NHR^{24}$, $NR_2^{24}$, $NHCOR^{24}$, $NO_2$, SH, $SR^{24}$, $SOR^{24}$, $SO_3H$, $SO_3R^{24}$ or halogen. $R^{24}$ in the above substituents is alkyl, aralkyl or aryl.

It will be appreciated that the monosaccharide portion of the novel chiral Schiff bases which, in general formula (V), are shown in the cyclic hemiacetal or hemiketal form, may exist in equilibrium with the corresponding open chain form having a free carbonyl group. Moreover, while the monosaccharide may exist in the furanose form (5-membered ring), the pyranose form is usually more stable for the free monosaccharide.

Preferably r is 0, q is 1, $R^{13}$, $R^{14}$ and $R^{16}$ are hydrogen, $R^1$ is $-CH_2OR^{22}$, $R^{17}$ is lower alkyl, e.g. methyl, $L^1$ is hydrogen and (a) $J^1$ is

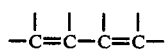

and $K^1$ is nitrogen or

i.e. the aromatic system in general formula (V) is pyrid-2-yl or 2-hydroxyphenyl, or (b) $J^1$ is

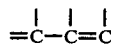

and $K^1$ is $-NH-$, i.e. the aromatic system in general formula (V) is pyrrol-2-yl.

Particularly preferably p is 0, $R^{21}$ is hydrogen, $J^1$ is

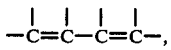

$L^1$ is hydrogen, s is 4 and $K^1$ is nitrogen or COH.

More particularly preferably chiral Schiff bases the transition metal complexes of which may be used in the process of the present invention have the general structure represented by the modified Haworth projection formula:

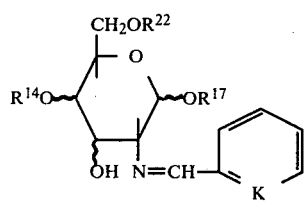

where $R^{17}$ is lower alkyl, $R^{14}$ and $R^{22}$ are both hydrogen or together form a divalent hydrocarbon group and K is nitrogen or COH; since we have found that these chiral Schiff bases in which the pyranose ring has the configuration at C2 (the carbon bonded to the carbon of the acetal or hemiacetal group) specified in general formula (V) form metal complexes which, when employed as catalysts in the process according to the present invention often give preferentially cyclopropane carboxylic acid esters having the IR configuration.

Examples of specific amino-monosaccharides from which, or from derivatives of which, novel chiral Schiff bases of formula(XV) may be prepared, include inter alia 2-amino-2-deoxy-D-glucose, 2-amino-2-deoxy-D-allose, 2-amino-2-deoxy-D-galactose, 2-amino-2-deoxy-D-altrose, 2-amino-2-deoxy-D-mannose, 2-amino-2-deoxy-D-ribose and 2-amino-2-deoxy-D-xylose.

Examples of specific carbonyl compounds from which novel chiral Schiff bases of formula (XV) may be prepared include inter-alia salicylaldehyde, 2-hydroxy-1-naphthaldehyde, pyridine-2-carboxaldehyde, pyridine-2-carboxaldehyde-N-oxide, 2-acetylpyridine, quinoline-8-carboxaldehyde, pyridoxal and pyrrole-2-carboxaldehyde.

The catalysts of class (v) in which a transition metal is coordinated with a chiral Schiff base of formula (XV) have the general formula:

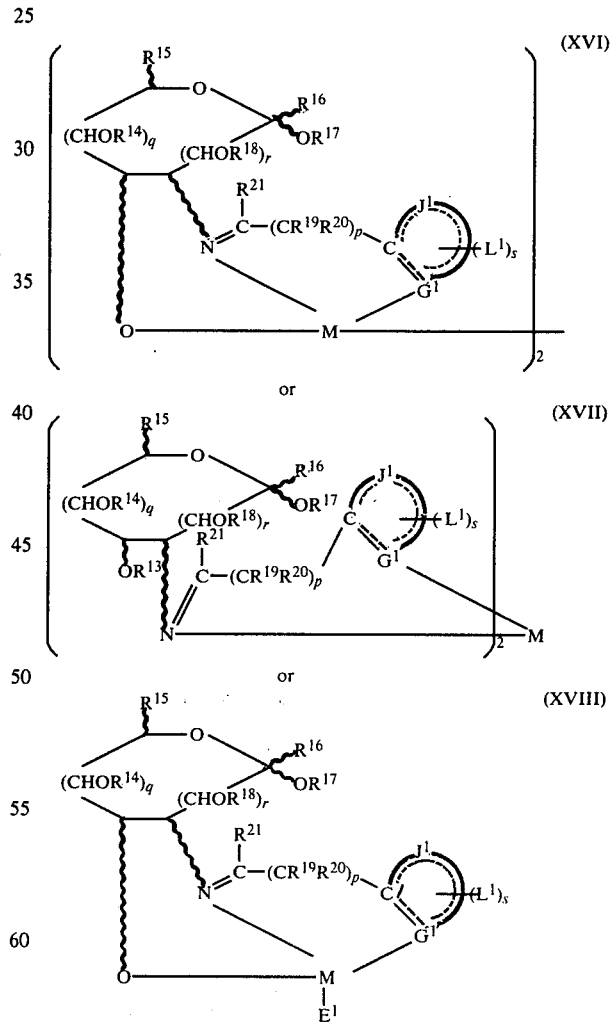

wherein $R^{13}$, $R^{14}$ and $R^{18}$ which may be the same or different, are hydrogen or lower alkyl, except that at least one of $R^{13}$ and $R^{18}$ is hydrogen;

$R^{15}$ is hydrogen, a sugar derivative or —CH$_2$OR$^{22}$, in which R$^{22}$ is hydrogen, lower alkyl or together with R$^{14}$ forms a divalent hydrocarbon group;

$R^{16}$ is hydrogen or —CH$_2$OR$^{22}$ in which R$^{22}$ is hydrogen or lower alkyl;

$R^{17}$ is hydrogen, lower alkyl or a sugar derivative;

$R^{19}$ and R$^{20}$, which may be the same or different, are hydrogen or lower alkyl, or where p is 1, may with the cyclic ring to which CR$^{19}$R$^{20}$ is attached form a fused ring system;

$R^{21}$ is hydrogen, alkyl, aralkyl or aryl;

$E^1$ is a monodentate neutral ligand;

$G^1$ is nitrogen,

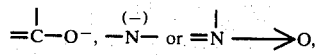

$J^1$ is a chain of 3 or 4 atoms consisting either exclusively of carbon atoms or carbon atoms together with one or more hetero atoms which may be the same or different, which chain with the group —C═══G$^1$— forms an aromatic system, $L^1$, each of which may be the same or different, represents a substituent attached to a carbon atom in the chain J$^1$ and is hydrogen, alkyl, aralkyl, aryl or a substituent containing a hetero-atom, or two groups L$^1$ together with the ring to which they are attached form a fused ring system;

M is a metal from the first or second series of the main group of transition metals;

r is 0 or 1;

q is 0, 1 or 2 provided that q+r are 1, 2 or 3;

p is 0, 1 or 2 and s is the number of carbon atoms in the chain J$^1$.

In the above definition the term "lower alkyl" means an alkyl group having 1 to 4 carbon atoms.

By transition metal we mean a metal which, in any one of its commonly occurring oxidation states, has a partly filled d shell only. In the first series the partly filled d shell is 3d and in the second series the partly filled d shell is 4d.

Preferably the metal is copper(II), chromium(II), manganese(II), iron(II) and (III), cobalt(II), nickel(II) or palladium(II). Particularly preferably the metal is copper(II).

It will be appreciated that complexes according to the general formula (XVI) are bi-nuclear and complexes according to the general formulae (XVII) and (XVIII) are mononuclear; and that in the complexes according to the general formulae (XVI) and (XVIII) the Schiff base behaves as a tridentate ligand and that in complexes according to the general formula (XVII) the Schiff base behaves as a bidentate ligand.

Ligands $E^1$ are suitably Lewis bases, examples are tertiary phosphine oxides and amines such as pyridine.

A preferred group of metal complexes for use in the invention are those according to general formula (XVII) given above since they give a higher enantiomer excess in the reaction of a monoene of formula (II) with a diazoacetate than given by the metal complexes according to general formulae (XVI) and (XVIII).

In metal complexes according to the general formulae (XVI), (XVII) or (XVIII), preferably r is 0 and q is 1, R$^{14}$ and R$^{16}$ are hydrogen, R$^{15}$ is CH$_2$OR$^{22}$, R$^{17}$ is lower alkyl, e.g. methyl, L$^1$ is hydrogen and J$^1$ is

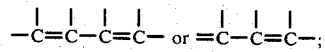

particularly preferably p is 0, R$^{21}$ is hydrogen, J$^1$ is

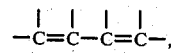

$L^1$ is hydrogen, s is 4 and G$^1$ is nitrogen or

more particularly preferably the metal complex has the general structure represented by the modified Howarth projection forulae:

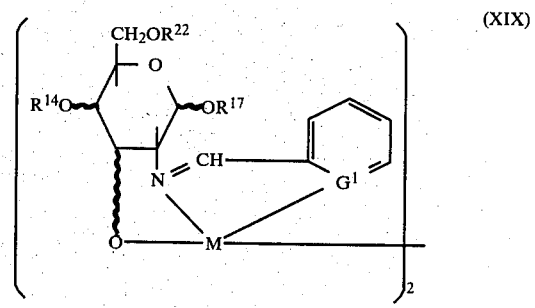

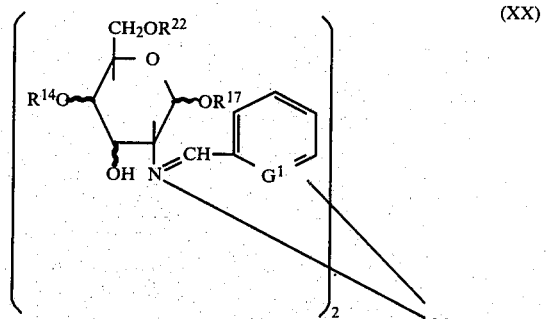

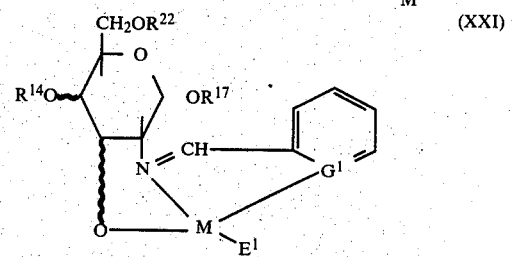

where R$^{17}$ is lower alkyl, e.g. methyl, R$^{14}$ and R$^{22}$ are hydrogen, or together form a divalent hydrocarbon radical, G$^1$ is nitrogen or

and $E^1$ has the previously defined meaning.

Where, in the general formulae (XVI)–(XXI), G$^1$ is nitrogen or NO, the metal complex carries a positive charge and an anion is necessary to provide an electrically neutral compound. The anions associated with the metal cation may be inorganic or organic, provided that they are derived from strong acids having a pKa value less than 2.5.

The anions should not be oxidising or reducing agents or otherwise chemically reactive with diazoacetic esters or other materials used in the process according to the present invention. Suitable anions include, inter alia, halide, tetrafluoroborate, methosulphate, bisulphate, sulphate, aromatic sulphonate, fluorosilicate and tetraphenylborate.

Amino-sugars useful for the preparation of chiral Schiff bases, the transition metal complexes of which may be used in the process of the present invention, may be naturally occurring, e.g. D-glucosamine or D-mannosamine, or they may be prepared from monosaccharides or from naturally occurring aminomonosaccharides.

The chiral Schiff bases of class (v) may be obtained by reacting the appropriate amino-sugar with a carbonyl compound having the formula:

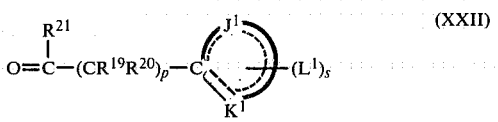
(XXII)

wherein $R^{19}$, $R^{20}$, $R^{21}$, $J^1$, $K^1$, $L^1$, p and s have the previously defined meanings.

The reaction is preferably carried out in the presence of an inert solvent. Suitable solvents include aromatic hydrocarbons, e.g. toluene; alcohols, e.g. methanol, and halogenated hydrocarbons, e.g. 1,2-dichloroethane and chloroform.

Various methods are available for preparing the metal complexes of chiral Schiff bases of class (v). The Schiff base may be reacted with a suitable salt of the appropriate metal. The amino-monosaccharide may be reacted with an appropriate metal keto or aldehyde complex, e.g. bis(salicylaldehydato)copper (II). The preferred method involves reacting the Schiff base with an appropriate metal-keto or metal-aldehyde complex; the metal complexes obtained by this method tend to be more selective than those obtained by other methods.

Catalysts of class (v) and their preparation are the subject of a co-pending United Kingdom Patent Application.

With regard to catalysts of class (vi) derived from a chiral Schiff base having the general formula (VA), examples of alkyl groups represented by $R^{25}$, $R^{26}$, $R^{27}$ and $R^{30}$ are methyl, ethyl, n-propyl, iso-propyl, n-butyl, iso-butyl, sec-butyl, tert-butyl, n-pentyl, n-hexyl, cyclohexyl, n-octyl, 2-ethylhexyl, n-decyl and n-dodecyl. Where $R^{25}$, $R^{26}$ or $R^{27}$ include one or more hetero atoms, specific examples include OH, $OR^{33}$, $OCOR^{33}$, CHO, $COR^{33}$, $CO_3H$, $CO_2R^{33}$, CN, $CONH_2$, $NH_2$, $NHR^{33}$, $NR_2^{33}$, $NHCOR^{33}$, $NO_2$, SH, $SOR^{33}$, $SO_3H$, $SO_3R^{33}$ or a halogen atom. $R^{33}$ in the above substituents is alkyl, aralkyl or aryl.

Examples of aralkyl groups represented by $R^{30}$ are benzyl and 2-phenylethyl.

Exmples of substituents $R^{31}$ and $R^{32}$ in general, formula (VB) are methyl, ethyl, propyl, iso-propyl, butyl, iso-butyl, sec-butyl, tert-butyl, octyl, cyclohexyl, cyclohexylmethyl, benzyl, benzhydryl, 2,2-diphenylethyl, phenyl, tolyl and naphthyl. In compounds of formula (VA) containing groups $J^2$ and $K^2$ represented by formula (VB), preferably $R^{25}$, $R^{26}$, $R^{27}$ and $R^{30}$ are hydrogen, $R^{32}$ is a substituted phenyl group and n is 0.

It is also preferred that $R^{32}$ represents a phenyl group having a substituent at the 2-position or substituents at the 2,5- or 2,6-positions. Examples of such substituted phenyl groups are those given for the group $R^8$ in the catalyst class (iv) above.

It will be appreciated that the monosaccharide substituents represented by $J^2$ and $K^2$ which, in formula (VC), are shown in the cyclic hemiacetal or hemiketal form may exist in equilibrium with the corresponding open-chain form having a carbonyl group. Moreover, while the monosaccharide may exist in the furanose form (five membered ring) the pyranose form is usually more stable for the free monosaccharide.

Where groups $J^2$ and $K^2$ are represented by formula (VC) preferably $r=0$, $q=1$, $R^{13}$, $R^{14}$ and $R^{16}$ are hydrogen, $R^{15}$ is $-CH_2OR^{22}$, $R^{17}$ is lower alkyl, e.g. methyl and particularly preferably $J^2$ and $K^2$ have the general structure represented by the modified Howarth projection formula:

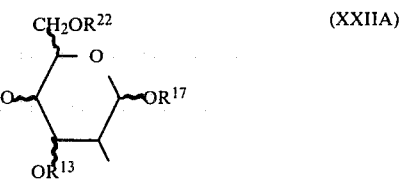
(XXIIA)

wherein $R^{17}$ is lower alkyl, $R^{13}$ is hydrogen and $R^{14}$ and $R^{22}$ are both hydrogen or together form a divalent hydrocarbon group, since it has been found that these chiral Schiff bases in which the pyranose ring has the configuration at C2 (the carbon bonded to the carbon acetal or hemiacetal group) specified in general formula (XXIIA) form metal complexes which, when employed as catalysts in the process according to the present invention often give preferentially cyclopropane carboxylic acid esters having the IR configuration.

The chiral Schiff bases, the metal complexes of which form the catalysts of class (vi) above, may be obtained by reacting an amino monosaccharide having the formula:

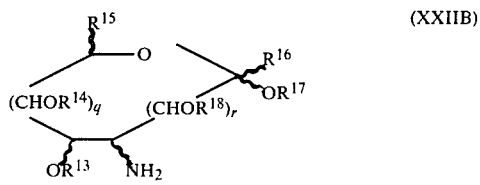
(XXIIB)

or a chiral amino alcohol having the formula:

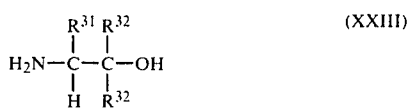
(XXIII)

with a dicarbonyl compound having the formula

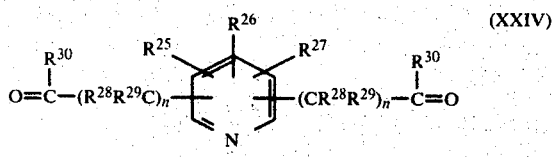

(XXIV)

wherein $R^{13}$, $R^{14}$, $R^{15}$, $R^{16}$, $R^{17}$, $R^{18}$, $R^{25}$, $R^{26}$, $R^{27}$, $R^{28}$, $R^{29}$, $R^{30}$, $R^{31}$, $R^{32}$ and n, q and r have the previously defined meanings.

The reaction is preferably carried out in the presence of an inert solvent in which the Schiff base is insoluble and is effected near the reflux temperature of the solvent.

Suitable solvents include aromatic hydrocarbons, e.g. toluene; alcohols, e.g. methanol, and halogenated hydrocarbons, e.g. 1,2-dichloroethane and chloroform.

Examples of specific compounds of formula (XXIV) which may be used to prepare the Schiff bases of formula (VA) are pyridine-2,6-dicarboxaldehyde and 2,6-diacetylpyridine.

Whilst the chiral amino alcohol of formula (XXIII) may be obtained by optical resolution of a mixture of enantiomers, preferably it is prepared from a chiral starting material. α-Amino acid esters are convenient starting materials and they may be converted into suitable chiral aminoalcohols by known methods using appropriate Grignard reagents. An example of an aminoalcohol of formula (XXIII) is 2-amino-1,1-di-(2-methoxyphenyl)-3-phenylpropan-1-ol.

The compounds of formula (VA) having an oxygen atom on the ring nitrogen may be obtained by oxidation of the corresponding compounds of formula (VA) in which the ring nitrogen is unsubstituted. A suitable oxidising agent for this purpose is hydrogen peroxide.

The catalysts of class (vi) in which a transition metal is coordinated with a chiral Schiff base are believed to have structures represented by the general formula:

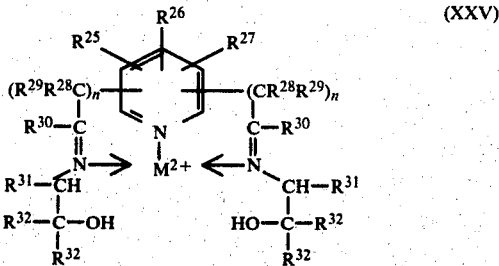

(XXV)

wherein $R^{25}$, $R^{26}$, $R^{27}$, $R^{28}$, $R^{29}$, $R^{30}$, $R^{31}$, $R^{32}$ and n have the previously defined meanings and M is a metal from the first or second series of the main group of transition metals, as defined in connection with catalysts of class (iv).

Preferably the metal is copper(II), chromium(II), manganese(II), iron(II), iron(III), cobalt(II), nickel(II) or palladium(II). Particularly preferably the metal is copper(II). It will be appreciated that in chiral metal complexes as defined in formula (XXV) the metal carries a positive charge and that an anion is necessary to provide an ionically neutral compound. The anions associated with the metal complexes may be inorganic or organic provided that they are derived from strong acids having a pKa value less than 2.5.

The anions should not be oxidising or reducing agents or otherwise chemically reactive with diazoacetic esters or other materials used in the process according to the invention. Suitable anions include, inter alia; halide, tetrafluoroborate, methosulphate, bisulphate, sulphate, aromatic sulphonate, fluorosilicate and tetraphenylborate.

Various methods are available for preparing the metal complexes of the chiral Schiff bases of formula (VA). The Schiff base may be reacted with a suitable salt of the appropriate metal. The aminoalcohol of formula (XXIII) may be reacted with an appropriate metal complex of an aldehyde or ketone of formula (XXIV); or the Schiff base may be reacted with an appropriate metal ketone or aldehyde complex; the metal complexes obtained by this latter method tend to be more selective than those obtained by other methods.

Catalysts of class (vi) and their preparation are the subject of a copending United Kingdom Patent Application.

The preparation of typical chiral Schiff bases, and of metal complexes of chiral Schiff bases of class (v) for use according to the process of the present invention, is described below:

A. Preparation of methyl N-salicylidene-4,6-O-benzylidene-2-amino-2-deoxy-α-D-altropyranoside.

Methyl 4,6-O-benzylidene-2-amino-2-deoxy-αD-altropyranoside (0.7 g.) (prepared by the method of W. H. Meyer and G. H. Robertson, *J. Amer. Chem. Soc.* 1943, 65, 8) and salicylaldehyde (0.3 g.) in toluene (50 ml.) were refluxed for 2 hours. The reaction mixture was cooled and the precipitate was filtered off. Recrystallisation from methanol/petroleum ether (b.p. 40°–60° C.) gave methyl N-salicylidene-4,6-O-benzylidene-2-amino-2-deoxy-α-D-altropyranoside (m.p. 218° C.).

|  | C | H | N |
|---|---|---|---|
| Elemental analysis for $C_{21}H_{23}O_6N$ |  |  |  |
| Found: | 65.38 | 5.82 | 3.28 |
| Calculated | 65.45 | 5.97 | 3.60 |

B. By similar procedure to that described in A above, other chiral Schiff bases were prepared from methyl 4,6-O-benzylidene-2-amino-2-deoxy-α-D-altropyranoside and the appropriate carbonyl compounds as follows:

(a) Methyl N-(2-hydroxynaphthylidene)-4,6-O-benzylidene-2-amino-2-deoxy-α-D-altropyranoside (m.pt. 243° C.) was prepared from 2-hydroxynaphth-1-aldehyde.

|  | C | H | N |
|---|---|---|---|
| Elemental analysis for $C_{25}H_{25}O_6N$ |  |  |  |
| Found: | 68.00 | 5.96 | 2.79 |
| Calculated | 68.97 | 5.75 | 3.22 |

(b) Methyl N-(2-pyridinylidene)-4,6-O-benzylidene-2-amino-2-deoxy-α-D-altropyranoside was prepared from pyridine-2-carboxyaldehyde.

|  | C | H | N |
|---|---|---|---|
| Elemental analysis for $C_{20}H_{22}N_2O_5$ |  |  |  |
| Found: | 63.82 | 6.07 | 6.96 |
| Calculated | 64.86 | 5.95 | 7.57 |

C. Preparation of chiral Schiff bases from methyl 4,6-O-benzylidene-2-amino-2-deoxy-β-D-altropyranoside (prepared by the method of W. H. Mayer and G. J. Robertson, *J. Amer. Chem. Soc.* 1943, 65, 8).

(a) The amino-monosaccharide (0.45 g.) and salicylaldehyde (0.2 g.) were refluxed in ethanol (30 ml.) for 2 hours. The solvent was evaporated off and the residual methyl N-salicylidene-4,6-O-benzylidene-2-amino-2-deoxy-β-D-altropyranoside had a m.pt. of 190°–200° C.

(b) The amino-monosaccharide (0.4 g.) and 2-hydroxynaphth-1-aldehyde (0.25 g.) were refluxed in ethanol (20 ml.) for 2 hours. The solvent was evaporated off and the residual methyl N-(2-hydroxynaphthylidene)-4,6-O-benzylidene-2-amino-2-deoxy-β-D-altropyranoside had a m.pt. of 115° C.

(c) The amino-monosaccharide (0.5 g.) and pyridine-2-carboxaldehyde (0.2 g.) were refluxed in methanol (20 ml.) for 2 hours. The solvent was evaporated off and the residual methyl N-(2-pyridinylidene)-4,6-O-benzylidene-2-amino-2-deoxy-β-D-altropyranoside had a m.pt. of 248° C.

D. Preparation of chiral Schiff bases from methyl 4,6-O-benzylidene-2-amino-2-deoxy-α-D-allopyranoside (prepared by the method of C. B. Barlow and E. A. Guthrie *J. Chem. Soc. (Part C)* 1967, 1196).

(a) The amino-monosaccharide (1.48 g.) and salicylaldehyde (0.74 g.) were refluxed in toluene (40 ml.) for 2½ hours. The solvent was evaporated off at reduced pressure and the residue crystallised to give methyl N-salicylidene-4,6-O-benzylidene-2-amino-2-deoxy-α-D-allopyranoside (1.38 g; m.pt. 188°–192° C.).

|  | C | H | N |
|---|---|---|---|
| Elemental analysis for $C_{21}H_{23}NO_6$ |  |  |  |
| Found: | 64.08 | 6.19 | 3.14 |
| Calculated | 65.45 | 5.97 | 3.64 |

(b) The amino-monosaccharide (0.70 g.) and pyridine-2-carboxaldehyde (0.27 g.) were refluxed in toluene (20 ml.) for 2½ hours. The solvent was evaporated off at reduced pressure and the residue was dried in vacuo to give methyl N-(2-pyridinylidene)-4,6-O-benzylidene-2-amino-2-deoxy-α-D-allopyranoside as a golden solid (0.68 g; m.pt. 54°–60° C.)

|  | C | H | N |
|---|---|---|---|
| Elemental analysis for $C_{20}H_{22}N_2O_5$ |  |  |  |
| Found: | 62.96 | 6.43 | 6.76 |
| Calculated | 64.86 | 5.94 | 7.57 |

E. Preparation of chiral Schiff bases from methyl 2-amino-2-deoxy-β-D-glucopyranoside (prepared by the method of A. Neuberger and R. P. Rivers, *J. Chem. Soc.* 1939, 122).

(a) The amino-monosaccharide (0.8 g.) and salicylaldehyde (0.55 g.) were heated at reflux in ethanol (50 ml.) for 2 hours. The reaction mixture was evaporated to dryness to leave methyl N-salicylidene-2-amino-2-deoxy-β-D-glucopyranoside as a yellow oil.

(b) The amino-monosaccharide (0.8 g.) and 2-hydroxy-1-naphthaldehyde were heated at reflux in ethanol (50 ml.) for 2 hours. The reaction mixture was evaporated to dryness to leave methyl N-(2-hydroxy-1-naphthylidene)-2-amino-2-deoxy-β-D-glucopyranoside as a green oil.

(c) The amino-monosaccharide (0.8 g.) and pyridine-2-carboxaldehyde (0.44 g.) were heated at reflux in ethanol (50 ml.) for 2 hours. The reaction mixture was evaporated to dryness to leave methyl N-(2-pyridinylidene)-2-amino-2-deoxy-β-D-glucopyranoside as a yellow solid.

F. Preparation of chiral Schiff bases from methyl 2-amino-2-deoxy-α-D-glucopyranoside (prepared by the method of A. Neuberger and R. P. Rivers, *J. Chem. Soc.* 1939, 122).

(a) The amino-monosaccharide (0.6 g.) and salicylaldehyde (0.38 g.) were heated at reflux in ethanol (50 ml.) for 2 hours. The reaction mixture was evaporated to dryness to leave methyl N-(salicylidene)-2-amino-2-deoxy-α-D-glucopyranoside as a yellow oil.

(b) The amino-monosaccharide (0.6 g.) and pyridine-2-carboxaldehyde (0.33 g.) were heated at reflux in ethanol (50 ml.) for 2 hours. The reaction mixture was evaporated to dryness to leave methyl N-(2-pyridinylidene)-2-amino-2-deoxy-β-D-glucopyranoside as a yellow oil.

G. Preparation of metal complexes of Schiff bases of methyl 4,6-O-benzylidene-2-amino-2-deoxy-α-D-altropyranoside.

(a) Methyl N-(2-hydroxynaphthylidene)-4,6-O-benzylidene-2-amino-2-deoxy-α-D-altropyranoside (0.435 g.) was added in portions over 1 hour with stirring to $Cu^{II}$ bis(salicylaldehyde) (0.153 g.) (prepared by reacting cupric chloride and sodium salicylaldehyde in water, extracting into toluene and evaporating) in methanol (10 ml). The reaction mixture was stirred for 3 hours and the mononuclear copper complex of the Schiff base was filtered off, m.pt. 218° C.,$[\alpha]D=+35°$.

|  | C | H | N |
|---|---|---|---|
| Elemental Analysis for $C_{50}H_{50}O_{12}N_2Cu$ |  |  |  |
| Found: | 63.79 | 4.79 | 2.70 |
| Calculated | 64.27 | 5.36 | 3.00 |

(b) Methyl N-(2-hydroxynaphthylidene)-4,6-O-benzylidene-2-amino-2-deoxy-α-D-altropyranoside (0.453 g.) and cupric acetate .H₂O (0.2 g.) were heated at reflux in methanol (20 ml.) for 30 minutes. The binuclear copper complex of the Schiff base was filtered off, dec.>250°,$[\alpha]_D=200°$.

|  | C | H | N |
|---|---|---|---|
| Elemental analysis for $C_{25}H_{25}O_6NCu$ |  |  |  |
| Found: | 59.80 | 5.25 | 1.90 |
| Calculated | 60.18 | 5.02 | 2.81 |

(c) Cupric chloride—2H₂O (0.170 g.) in water (4 ml.) was added slowly to methyl N-(2-pyridinylidene)-4,6-O-benzylidene-2-amino-2-deoxy-α-D-altropyranoside (1.23 g.). Water (2 ml.) and methanol (6 ml.) were added and the mixture was stirred for 30 minutes. Sodium fluoroborate (0.2 g.) in water (1 ml.) was added and stirring was continued for 10 minutes. The solvent was evaporated off to leave the mononuclear copper complex of methyl N-(2-pyridinylidene)-4,6-O-benzylidene-2-amino-2-deoxy-α-D-altropyranoside as a green residue m.pt. 170° C.

(d) Methyl N-salicylidene-4,6-O-benzylidene-2-amino-2-deoxy-α-D-altropyranoside (0.385 g.) was added in portions with stirring over 1 hour to $Cu^{II}$ bis-(salicylaldehyde) (0.153 g.) in methanol (10 ml.). The reaction mixture was stirred for 1 hour and a solid was filtered off. Evaporation of the filtrate left a mononuclear copper complex of methyl N-salicylidene-4,6-O-benzylidene-2-amino-2-deoxy-α-D-altropyranoside, m.pt. 190°-205° C. $[\alpha]_D = 300°$.

|  | C | H | N |
|---|---|---|---|
| Elemental analysis for $C_{42}H_{44}N_2O_{12}Cu$ |  |  |  |
| Found: | 62.90 | 5.33 | 2.81 |
| Calculated | 60.60 | 5.29 | 3.37 |

(e) Methyl 4,6-O-benzylidene-2-amino-2-deoxy-α-D-altropyranoside (0.56 g.) in methanol (10 ml.) was added dropwise with stirring to a suspension of $Cu^{II}$ bis(salicylaldehyde) (0.154 g.) in methanol (5 ml.). The reaction mixture was stirred for 3 hours and then filtered.

(f) Methyl N-salicylidene-4,6-O-benzylidene-2-amino-2-deoxy-α-D-altropyranoside (0.385 g.) and cupric acetate .H₂O (0.2 g.) were heated under reflux in methanol (10 ml.) for 10 minutes. The methanol was evaporated off and the residue was extracted with toluene. The toluene extract was washed with a saturated aqueous sodium bicarbonate solution, then with water, dried and the toluene evaporated off to leave a binuclear copper complex of methyl N-salicylidene-4,6-O-benzylidene-2-amino-2-deoxy-α-D-altropyranoside, m.pt. 188° C. $[\alpha]_D + 530°$

|  | C | H | N |
|---|---|---|---|
| Elemental analysis for $C_{21}H_{21}NO_6Cu$ |  |  |  |
| Found: | 52.00 | 5.32 | 2.20 |
| Calculated | 56.30 | 4.92 | 3.13 |

H. Preparation of metal complexes of Schiff bases of methyl 4,6-O-benzylidene-2-amino-2-deoxy-β-D-altropyranoside.

(a) Methyl N-salicylidene-4,6-O-benzylidene-2-amino-2-deoxy-β-D-altropyranoside (0.35 g.) was added in portions over 1 hour with stirring to $Cu^{II}$bis(salicylaldehyde) (0.14 g.) (prepared as in G) in methanol (10 ml.) at 20° C. The reaction mixture was stirred for 2 hours and a solid was filtered off. The filtrate was evaporated to dryness to leave a copper complex of the Schiff base.

(b) Methyl N-(2-hydroxynaphthylidene)-4,6-O-benzylidene-2-amino-2-deoxy-β-D-altropyranoside (0.5 g.) and $Cu^{II}$ bis(salicylaldehyde) were reacted as above to give a copper complex of the Schiff base.

(c) Cupric chloride .2H₂O (0.069 g.) in water (2 ml.) was added slowly with stirring to methyl N-(2-pyridinylidene)-4,6-O-benzylidene-2-amino-2-deoxy-β-D-altropyranoside (0.5 g.) in methanol (10 ml.). The reaction mixture was stirred for 1 hour, sodium fluoroborate (0.17 g.) was added and stirred continued for a further 30 minutes. The solvent was removed.

I. Preparation of metal complexes of Schiff bases of methyl 4,6-O-benzylidene-2-amino-2-deoxy-α-D-allopyranoside.

(a) Methyl N-salicylidene-4,6-O-benzylidene-2-amino-2-deoxy-α-D-allopyranoside (0.65 g.) and cupric acetate .H₂O (0.24 g.) were heated at reflux in ethanol (10 ml.) for 10 minutes. The ethanol was evaporated off and the residue was dissolved in toluene. The toluene solution was washed with saturated aqueous sodium bicarbonate solution, then water, dried and evaporated. The residue was washed with methanol and dried to give a binuclear copper complex of methyl N-salicylidene-4,6-O-benzylidene-2-amino-2-deoxy-α-D-allopyranoside (0.3 g.) as a deep green solid.

(b) Methyl 4,6-O-benzylidene-2-amino-2-deoxy-α-D-allopyranoside (0.7 g.) in methanol (10 ml.) was added dropwise with stirring over 1 hour to a suspension of $Cu^{II}$ bis(salicylaldehyde) (0.38 g.) in methanol (10 ml.). The reaction mixture was stirred for 1 hour and a solid was filtered off. The filtrate was evaporated to dryness to leave a mononuclear copper complex of methyl N-salicylidene-4,6-O-benzylidene-2-amino-2-deoxy-α-D-allopyranoside as a green solid (0.5 g.).

J. Preparation of metal complexes of Schiff bases of methyl 2-amino-2-deoxy-β-D-glucopyranoside.

(a) Methyl N-salicylidene-2-amino-2-deoxy-β-D-glucopyranoside (1.15 g.) and $Cu^{II}$ bis(salicylaldehyde) (0.4 g.) were stirred in methanol (10 ml.) for 2 hours. The reaction mixture was evaporated to dryness to leave a mononuclear copper(II) complex of methyl N-salicylidene-2-amino-2-deoxy-β-D-glucopyranoside.

(b) Methyl N-(2-hydroxy-1-naphthylidene)-2-amino-2-deoxy-β-D-glucopyranoside (1.40 g.) and $Cu^{II}$ bis(salicylaldehyde) (0.4 g.) were stirred in methanol (10 ml.) for 2 hours. The reaction mixture was evaporated to dryness to leave a mononuclear copper(II) complex of methyl N-(2-hydroxy-1-naphthylidene)-2-amino-2-deoxy-β-D-glucopyranoside.

(c) Cupric chloride .2H₂O (0.17 g.) in water (4 ml.) was added to methyl N-(2-pyridinylidene)-2-amino-2-deoxy-β-D-glucopyranoside (1.20 g.) in methanol (10 ml.). The reaction mixture was stirred for 1 hour, sodium fluoroborate (0.4 g.) was added and stirring was continued for a further hour. The reaction mixture was evaporated to dryness to leave a mononuclear copper-(II) complex of methyl N-(2-pyridinylidene)-2-amino-2-deoxy-β-D-glucopyranoside.

K. Preparation of metal complexes of Schiff bases of methyl 2-amino-2-deoxy-α-D-glucopyranoside.

(a) Methyl N-salicylidene-2-amino-2-deoxy-α-D-glucopyranoside (0.85 g.) and $Cu^{II}$ bis(salicylaldehyde) (0.3 g.) were stirrred in methanol for 2 hours. The reaction mixture was evaporated to dryness to leave a mononuclear copper(II) complex of methyl N-salicylidene-2-amino-2-deoxy-α-D-glucopyranoside.

(b) Cupric chloride .2H₂O (0.12 g.) in water (3 ml.) was added to methyl N-(2-pyridinylidene)-2-amino-2-deoxy-α-D-glucopyranoside (0.90 g.) in methanol (3 ml.). The reaction mixture was stirred for 1 hour, sodium fluoroborate (0.3 g.) was added and stirring was continued for a further 2 hours. The reaction mixture was evaporated to dryness to leave a mononuclear copper(II) complex of methyl N-(2-pyridinylidene)-2-amino-2-deoxy-α-D-glucopyranoside.

The invention is illustrated by the following Examples, in which all percentages are by weight.

EXAMPLE 1

2,2-Dichloro-5-methyl-1,1,1-trifluorohex-4-ene (12 milli-mols) and rhodium (II) pivalate (0.02 mg atoms) were stirred together under nitrogen in a vessel connected to a manometer. A solution of ethyl diazoacetate in toluene (0.7 m.mol of diazoacetate per ml of solution) was added at a constant rate at 20° C. Nitrogen evolution was measured and the rate of diazoacetate addition was adjusted so that there was very little build-up of diazoacetate in the reaction mixture.

After 139 minutes, there had been formed 1.49 m.mol of nitrogen.

Gas-liquid chromatographic (GLC) analysis of the reaction mixture showed that ethyl 3-(2',2'-dichloro-3',3',3'-trifluoropropyl)-2,2-dimethylcyclopropane-1-carboxylate (0.91 m.mol) had been formed. The yield was 61% based on the nitrogen evolved. The analysis further showed that cis and trans-isomers of the product had been formed in the ratio 63:37 (the cis-isomer had the lower boiling point).

EXAMPLE 2

The procedure described in Example 1 was repeated except that the rhodium (II) pivalate was replaced by copper bronze (2.17 mg atoms) and the reaction temperature was 86° C.

After 40 minutes nitrogen (0.543 m.mol) had been evolved and ethyl 3(2',2'-dichloro-3',3',3'-trifluoropropyl)-2,2-dimethylcyclopropane-1-carboxylate (0.174 m.mol) had been formed in a yield of 34% based on the nitrogen evolved. The cis/trans isomer ratio of the product by GLC analysis was 64:36.

EXAMPLE 3

2,2-Dichloro-5-methyl-1,1,1-trifluorohex-4-ene (30 m.mol) and a mononuclear Cu (II) catalyst carrying a ligand derived from pyridine-2-carboxaldehyde and methyl 4,6-O-benzylidene-2-amino-2-deoxy-α-D-allopyranoside (equivalent to 2 mg atoms of copper) were treated with a toluene solution of ethyl diazoacetate (containing 0.7 m.mol of diazoacetate per ml of solution) at 80° C. Nitrogen (6.9 m.mol) was evolved, and the solution was found to contain ethyl 3-(2',2'-dichloro-3',3',3'-trifluoropropyl)-2,2-dimethylcyclopropane-1-carboxylate (0.52 m.mol) having a cis:trans isomer ratio of 80.4:19.6. The yield based on nitrogen evolved was 7.5%.

Part of the reaction mixture (1 ml) was treated with 2-d-octanol (200 mg) and tetra-n-butyltitanate (10 mg) under nitrogen at reflux temperature (heating bath temperature 150° C.) for 2 hours. Transesterification occurred to give the 2-d-octyl ester of 3-(2',2'-dichloro-3',3',3'-trifluoropropyl)-2,2-dimethylcyclopropane-1-carboxylic acid. Examination of the resulting mixture by GLC on a 5 m 1% LAC-2R-466 Column at 135° C., showed the presence of four 2-d-octyl esters. These are identified as cis IR, trans IR, cis IS and trans IS. The relative concentration were:

|  |  |
|---|---|
| cis IR | 57.8% |
| trans IR | 13.6% |
| cis IS | 22.6% |
| trans IS | 6.0% |

Thus the preferred cis IR isomer is formed in yield greater than the other three isomers combined. The catalyst used in this Example was prepared by reacting methyl 4,6-O-benzylidene-2-amino-2-deoxy-α-D-allopyranoside with pyridine-2-carboxaldehyde to give the Schiff base, which is converted into its copper (II) fluorocarborate complex following the method described in *Inorganic Chemistry*, 2, 1178 (1963).

EXAMPLE 4

2,2-Dichloro-5-methyl-1,1,1-trifluorohex-4-ene (5.0 g; 22.6 m.mol) and catalyst (prepared as described below) (0.219 g; 0.2 m.mol), equivalent to 0.2 mg atom Cu) were stirred at 50° C. under an atmosphere of nitrogen. A burette was charged with a solution comprising the same olefin (5.0 g), ethyl diazoacetate (5.4 ml of a standard toluene solution; 7.5 m.mol) and toluene (9.5 ml). This solution was added to the suspension of catalyst in olefin at a constant rate of approximately 1.3 ml per hour, and the nitrogen evolved during the reaction was collected. After 20 hours at 50° C. the addition of the diazoacetate/olefin solution was complete and the volume of nitrogen collected was 170 ml (approximately 100% of theoretical nitrogen evolved for total decomposition of the ethyl diazoacetate).

The reaction mixture was analysed by GLC (3% silicone OV 17; 2.7 m column) to determine the yield of cyclopropane (14%) and to find the approximate cis:-trans isomer ratio (between 68:32 and 64:36).

A further GLC analysis was carried out in order to estimate the relative yields of all four enantiomers produced during the reaction. The method was as follows:

An aliquot (1 ml) of the crude reaction mixture was refluxed with 2-d-octanol (200 mg) and tetra-n-butyl-titanate (10 mg) under an atmosphere of nitrogen to effect ester exchange. GLC analysis (1% LAC 2R 446; 5 m column) showed four peaks corresponding to the two cis and two trans diastereoisomeric 2-d-octyl esters. These are identified as cis IR, trans IR, cis IS and trans IS respectively. The isomer composition and cis:trans ratio were:

|  |  |  |
|---|---|---|
| cis:trans ratio |  | 66:34 |
| Composition: | cis IR | 47% |
|  | trans IR | 18% |
|  | cis IS | 19% |
|  | trans IS | 16% |

The catalyst used in this Example had the structure:

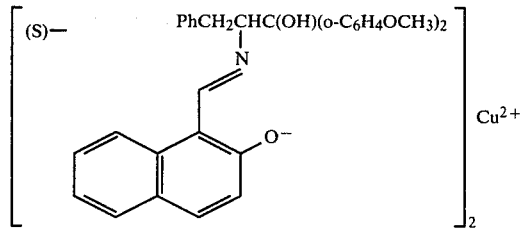

and was prepared as follows:

A suspension of bis(2-hydroxy-1-naphthaldehydato) copper (0.57 g; 1.4 mM) in methanol (10 ml) was stirred vigorously at room temperature whilst a solution of (S)-2-amino-1,1-di-(2-methoxyphenyl)-3-phenylpropan-1-ol (1.02 g; 2.8 mM) in methanol (10 ml) was added dropwise. The reaction mixture was stirred for a further one hour after the addition was complete and the resulting pale brown solid was collected by filtration. The product (0.82 g; 53%) had a melting point of 170° C.

EXAMPLE 5

The procedure described in Example 2 was repeated except that the 2,2-dichloro-5-methyl-1,1,1-trifluorohex-4-ene was replaced by 1,1,1-trichloro-4-methylpent-3-ene.

Analysis of the reaction mixture as described in Example 3 shows that the isomer distribution of the product, 2,2-dimethyl-3-(1',1',1'-trichloroethyl)cyclopropane-1-carboxylic acid ethyl ester, was as follows:

|  |  |
|---|---|
| cis IR | 28% |

| | |
|---|---|
| cis IS | 28% |
| trans IR | 22% |
| trans IS | 22% |

EXAMPLE 6

The procedure described in Example 1 was repeated except that the 2,2-dichloro-5-methyl-1,1,1-trifluorohex-4-ene was replaced by 1,1,1-trichloro-4-methyl-pent-3-ene.

Analysis of the reaction mixture as described in Example 3 showed that the isomer distribution of the product, 2,2-dimethyl-3-(1',1',1'-trichloroethyl)cyclopropane-1-carboxylic acid ethyl ester, was as follows:

| | |
|---|---|
| cis IR | 30% |
| cis IS | 30% |
| trans IR | 20% |
| trans IS | 20% |

EXAMPLE 7

The procedure described in Example 3 was repeated except that the 2,2-dichloro-5-methyl-1,1,1-trifluorohex-4-ene was replaced by 1,1,1-trichloro-4-methylpent-3-ene.

Analysis of the reaction mixture as described in Example 3 showed that the isomer distribution of the product, 2,2-dimethyl-3-(1',1',1'-trichloroethyl)cyclopropane-1-carboxylic acid ethyl ester, was as follows:

| | |
|---|---|
| cis IR | 33% |
| cis IS | 23% |
| trans IR | 25% |
| trans IS | 19% |

EXAMPLE 8

The procedure described in Example 4 was repeated except that the catalyst employed was a mononuclear copper(II) complex of the Schiff base derived from pyridine-2-carboxaldehyde and S-2-amino-1,1-di(2-methoxyphenyl)-3-phenylpropan-1-ol (equivalent to 0.2 mg atoms of copper; prepared as described below).

The yield and isomer ratio of the product were determined as described in Example 4, and the results are shown in the following Table, from which it can be seen that an enantiomeric excess of the cis IR enantiomer is obtained when the reaction of 2,2-dichloro-5-methyl-1,1,1-trifluorohex-4-ene with diazoacetatic acid ethyl ester is catalysed by a mononuclear copper(II) complex of a Schiff base notionally derived from an S-amino acid.

| | | Isomer ratio (%) | | | |
|---|---|---|---|---|---|
| Anion | Yield % | cis IR | cis IS | trans IR | trans IS |
| $BF_4$ | 9.4 | 36 | 24 | 17 | 23 |
| Cl | 7.0 | 43 | 26 | 12 | 19 |

The catalysts used in this Example were prepared as follows:

(i) Schiff base

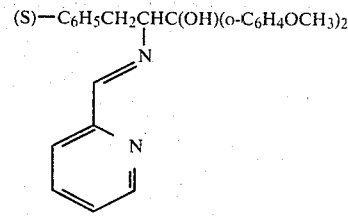

S-2-amino-1,1-bis(o-methoxyphenyl)-3-phenylpropan-1-ol (7.21 g; prepared by the method of A. McKenzie, R. Roger and G. O. Mills, J. Chem. Soc., 1926, 779) and freshly distilled pyridine-2-carboxaldehyde (2.35 g; 1.1 equivalents) were heated together under reflux in anhydrous toluene (50 ml.) for 4 hours. After cooling the reaction mixture to room temperature, the solution was dried over anhydrous magnesium sulphate, filtered, and evaporated in vacuo to afford a viscous brown syrup that was allowed to stand in dichloromethane-light petroleum (b.p. 46°-60° C.) overnight. Light brown cubic crystals separated and were filtered off, washed with cold light petroleum and dried (2.9 g.). The mother liquors were concentrated and two further crops of product were obtained (total yield 5.9 g; 65%). A small portion of the product was recrystallised from methanol and gave light brown crystals melting at 100°-105° C. The $^1$H nmr spectrum of the product was consistent with its proposed structure.

(ii) Copper complexes of Schiff base:

A portion of the Schiff base prepared as described in (i) above (0.828 g.) was dissolved in warm absolute alcohol (30 ml.) and a solution of cupric chloride dihydrate (0.156 g.) in distilled water (5 ml.) was added dropwise over 30 minutes. The solution was stirred at room temperature for 30 minutes and then divided into halves. One half of the solution was evaporated to small bulk and the resulting solid was filtered off, washed with distilled water and dried in vacuo to afford the chloride of the mononuclear copper(II) complex of the Schiff base derived from pyridine-2-carboxaldehyde and S-2-amino-1,1-di(2-methoxyphenyl)-3-phenylpropan-1-ol, which when recrystallised from dichloromethane/hexane melted at 170° C. with decomposition.

A solution of sodium fluoroborate (0.1 g.) in distilled water (5 ml.) was added to the other half of the solution. The mixture was evaporated to small bulk and the resulting solid was filtered off, washed with distilled water and dried in vacuo to afford the fluoroborate of the mononuclear copper(II) complex of the Schiff base derived from pyridine-2-carboxaldehyde and S-2-amino-1,1-di-(2-methoxyphenyl)-3-phenylpropan-1-ol having melting point 140°-142° C. (decomposition).

EXAMPLE 9

The procedure described in Example 8 was repeated except that the 2,2-dichloro-5-methyl-1,1,1-trifluorohex-4-ene and catalyst were replaced by, respectively, 1,1,1-trichloro-4-methylpent-3-ene and the cupric chloride complex of the same Schiff base, prepared as described in Example 8.

Analysis of the reaction mixture as described in Example 8 showed that the isomer distribution of the product, 2,2-dimethyl-3-(1',1',1'-trichloroethyl)cyclopropane-1-carboxylic acid ethyl ester, was as follows:

| | |
|---|---|
| cis IR | 46% |
| cis IS | 20% |
| trans IR | 15% |
| trans IS | 19% |

EXAMPLE 10

2,2-dichloro-5-methyl-1,1,1-trifluorohex-4-ene (1.25 g.) and a copper (II) complex of the Schiff base derived from pyridine-2,6-dicarboxaldehyde and S-2-amino-1,1-di(2-methoxyphenyl)-3-phenyl-1-propanol (0.04 mg atoms of copper), prepared as described below, were stirred in toluene (10.0 ml.) at 80° C. under an atmosphere of nitrogen. A burette was charged with a solution comprising the same olefin (1.25 g.) ethyl diazoacetate (1.4 ml. of a standard toluene solution; 1.94 m mole) and toluene (5.0 ml.). This solution was added to the solution of catalyst in olefin at a constant rate of approximately 1.3 ml. per hour, and the nitrogen evolved during the reaction was collected. After 20 hours at 80° C. the addition of the diazoacetate and olefin solution was complete and the volume of nitrogen collected was 45 ml. (approximately 100% of theoretical nitrogen evolved for total decomposition of the ethyl diazoacetate). The isomer ratio determined by glc analysis of the 2-d-octyl esters was:

| | |
|---|---|
| cis IR | 38% |
| cis IS | 22% |
| trans IR | 20% |
| trans IS | 20% |

From these results it can be seen that an enantiomeric excess of the IR isomers is obtained when the reaction of 2,2-dichloro-5-methyl-1,1,1-trifluorohex-4-ene with diazoacetic acid ethyl ester is catalysed by a copper complex of a Schiff base notionally derived from an S-amino acid.

The catalyst used in this Example was prepared as follows:

(i) Schiff base

A mixture of S-2-amino-1,1-di(2-methoxyphenyl)-3-phenyl-1-propanol (2.01 g.:5.54 m mole) (prepared by the method of A. McKenzie, R. Roger and G. O. Wills, *J. Chem. Soc.*, 1926, 779) and pyridine-2,6-dicarboxaldehyde (0.374 g.: 2.77 m mole) (prepared by the method of E. Papadopoulos, A. Jarrow and C. H. Issidorides, *J. Org. Chem.*, 1966, 31, 615) was heated at reflux in absolute alcohol (100 ml.) for 3 hours. After this time thin layer chromatography on silica gel using ether as eluant indicated a single product and no starting materials. Decolourising charcoal was added to the reaction mixture which was then heated for a further 1 hour. The reaction mixture was filtered and the filtrate was evaporated to approximately one-third of its volume. Addition of n-hexane to the concentrated filtrate gave a precipitate which was filtered off and dried (1.51 g;65% yield) m.pt. 160°–161° C. The $^1$Hnmr spectrum of the precipitate was consistent with the structure:

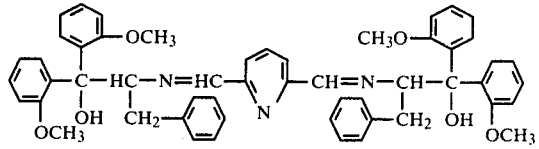

(ii) Copper (II) chloride derivative of Schiff base:

To a solution of the chiral Schiff base (0.447 g.:5.42 m mole) prepared as described in (i) above, in warm ethanol (20 ml.) was added dropwise with stirring over 15 minutes to a solution of copper (II) chloride dihydrate (0.092 g.:5.4 m mole) in water (5 ml.). During the addition the colour of the reaction mixture changed from pale yellow to green. The reaction mixture was evaporated to dryness and the resulting green solid was recrystallised from dichloromethane-hexane to give crystals (0.47 g.:90% yield), m.pt. 166°–168° C. (dec.).

We claim:

1. A process for the preparation of a compound of the formula:

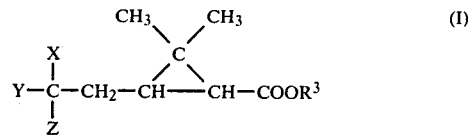

wherein $R^3$ is an alkyl, 3-phenoxybenzyl, α-cyano-3-phenoxybenzyl or α-ethyl-3-phenoxybenzyl group, Z is fluorine, chlorine or bromine, and X and Y, which may be the same or different, are fluorine, chlorine, bromine, lower alkyl or $Q(CF_2)_m$-, in which Q is hydrogen, fluorine or chlorine and m is 1 or 2, or

in which each of U, V and W are independently hydrogen, fluorine or chlorine except that where one of X and Y is a group of formula $Q(CF_2)_m$- where Q is as defined above, the other of X and Y is fluorine, chlorine or bromine or a group

as previously defined, characterised in that a compound having the formula:

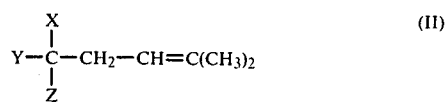

is reacted with an alkyl diazoacetate $N_2CH.COOR^3$, $R^3$, X, Y and Z having the previously defined meanings, in the presence of a catalyst selected from the following classes (i) to (vi):

(i) metallic copper, or a copper(II) salt,
(ii) rhodium(II) salts of carboxylic acids,
(iii) the copper complex of a chiral Schiff base having the formula:

$$\text{(III)}$$

$$R^4 \text{—} \underset{\underset{OH}{|}}{\bigcirc} \text{—} \underset{\underset{C}{\|}}{C} \text{=} N \text{—} CH(R^6) \text{—} C(R^7)(R^7) \text{—} OH$$

in which
R$^4$ is hydrogen, alkyl, aralkyl, aryl or a substituent containing a hetero atom, or R$^4$, when taken with the aromatic nucleus to which it is attached, forms a naphthalene ring system,
R$^5$ is hydrogen, alkyl, aralkyl or aryl and R$^6$ and R$^7$ are each alkyl, aralkyl or aryl,
(iv) the transition metal complex of a chiral Schiff base having the general formula:

$$HO\text{—}C(R^8)(R^8)\text{—}CH(R^9)\text{—}N\text{=}C(R^{10})\text{—}(CR^{11}R^{12})_n\text{—}C\underset{K}{\overset{J}{\diagup\diagdown}}(L)_m \quad \text{(IV)}$$

wherein
R$^8$ and R$^9$, which may be the same or different, are alkyl, aralkyl or aryl;
R$^{10}$ is hydrogen or lower alkyl, aryl, aralkyl or alkaryl,
R$^{11}$ and R$^{12}$, which may be the same or different are hydrogen or lower alkyl, or where n is 1, may with the cyclic system to which CR$^{11}$R$^{12}$ is attached, form a fused ring system,
J is a chain of 3 or 4 atoms consisting either exclusively of carbon atoms or of carbon atoms together with one or more hetero-atoms which may be the same or different, which chain with the group —C----K— forms an aromatic system,
K is nitrogen, N→O or —NH—,
L, each of which may be the same or different, represents a substituent attached to a carbon atom in the chain J and is hydrogen, alkyl, aralkyl, aryl or a substituent containing a heteroatom, or two groups L together with the ring to which they are attached, form a fused ring system,
n is 0, 1 or 2, and m is the number of carbon atoms in the chain J,
(v) the transition metal complex of a chiral Schiff base having the general formula:

$$\text{(V)}$$

$$\begin{array}{c} R^{15} \\ \diagup\text{—}O \\ (CHOR^{14})_q \quad \diagdown R^{16} \\ |\quad OR^{17} \\ (CHOR^{18})_r \\ | \\ R^{21} \\ | \\ OR^{13} \quad N\text{=}C\text{—}(CR^{19}R^{20})_p\text{—}C\underset{K^1}{\overset{J^1}{\diagup\diagdown}}(L^1)_s \end{array}$$

wherein

R$^{13}$, R$^{14}$, and R$^{18}$, which may be the same or different, are hydrogen or lower alkyl, except that at least one of R$^{13}$ and R$^{18}$ is hydrogen,
R$^{15}$ is hydrogen, a sugar derivative or —CH$_2$OR$^{22}$ in which R$^{22}$ is hydrogen, lower alkyl or together with R$^{14}$ forms a divalent hydrocarbon group,
R$^{16}$ is hydrogen or —CH$_2$OH,
R$^{17}$ is hydrogen, lower alkyl or a sugar derivative,
R$^{19}$ and R$^{20}$, which may be the same or different, are hydrogen or lower alkyl, or where p is 1, may with the cyclic system to which CR$^{19}$R$^{20}$ is attached form a fused ring system,
R$^{21}$ is hydrogen, alkyl, aralkyl or aryl,
J$^1$ is a chain of 3 or 4 atoms consisting either exclusively of carbon atoms or of carbon atoms together with one or more hetero atoms which may be the same or different, which chain with the group —C----K— forms an aromatic system,
K is C-OH, nitrogen, N→O or —NH—,
L$^1$, each of which may be the same or different, represents a substituent attached to a carbon atom in the chain J$^1$ and is hydrogen, alkyl, aralkyl, aryl or a substituent containing a heteroatom, or two groups L$^1$ together with the ring to which they are attached form a fused ring system,
r is 0 or 1,
q is 0, 1 or 2, provided that q+r is 1, 2 or 3,
p is 0, 1 or 2, and
s is the number of carbon atoms in the chain J$^1$, and
(vi) the transition metal complex of a chiral Schiff base having the general formula:

$$\text{(VA)}$$

$$J^2N\text{=}C(R^{30})\text{—}(R^{29}R^{28}C)_n\text{—}\underset{N}{\bigcirc}(R^{25})(R^{26})(R^{27})\text{—}(CR^{28}R^{29})_n\text{—}C(R^{30})\text{=}NK^2$$

wherein
R$^{25}$, R$^{26}$ and R$^{27}$, which may be the same or different, are hydrogen, alkyl, aralkyl, aryl, a substituent containing a hetero atom, or two of R$^{25}$, R$^{26}$ and R$^{27}$ together with the pyridine ring from a fused ring system,
R$^{28}$ and R$^{29}$, which may be the same or different, are hydrogen, lower alkyl, or, where n is 1, may with the pyridine ring to which C$^{28}$R$^{29}$ is attached, form a fused ring system,
R$^{30}$ is hydrogen, alkyl, aralkyl or aryl,
n is 0, 1 or 2
and J$^2$ and K$^2$, which may be the same or different, are groups of the formulae:

$$\text{(VB)}$$

$$-\underset{\underset{H}{|}}{C}(R^{31})\text{—}\underset{\underset{R^{32}}{|}}{C}(R^{32})\text{—}OH$$

or

-continued

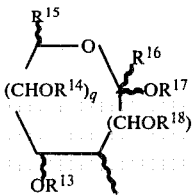
(VC)

in which $R^{31}$ and $R^{32}$, which may be the same or different, are alkyl, aralkyl or aryl, and $R^{13}$, $R^{14}$, $R^{15}$, $R^{16}$, $R^{17}$, $R^{18}$, q and r have the previously defined meanings, and the corresponding compounds having an oxygen atom attached to the pyridine ring nitrogen.

2. A process as claimed in claim 1 characterised in that the catalysts of class (iv) have one of the general formulae:

(XIII)

(XIV)

(XIVA)

in which $R^8$, $R^9$, $R^{10}$, $R^{11}$, $R^{12}$, J, L, m and n have the meanings defined in claim 1, E is a monodentate neutral ligand, M is a metal from the first or second series of the main group of transition metals and G is $=N-$,

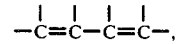

or $-N-$.

3. A process as claimed in claim 2 characterised in that the catalyst is a catalyst of formula (XIV) in which $R^8$ is substituted phenyl, $R^{10}$ is hydrogen, J is $$-\overset{|}{C}=\overset{|}{C}-\overset{|}{C}=\overset{|}{C}-,$$

G is nitrogen, L is hydrogen and n is 0.

4. A process as claimed in claim 1 characterised in that the catalysts of class (v) have one of the general formulae:

(XVI)

or (XVII)

or (XVIII)

wherein
- $R^{13}$, $R^{14}$ and $R^{18}$ which may be the same or different, are hydrogen or lower alkyl, except that at least one of $R^{13}$ and $R^{18}$ is hydrogen;
- $R^{15}$ is hydrogen, a sugar derivative or $-CH_2OR^{22}$, in which $R^{22}$ is hydrogen, lower alkyl or together with $R^{14}$ forms a divalent hydrocarbon group;
- $R^{16}$ is hydrogen or $-CH_2OR^{22}$ in which $R^{22}$ is hydrogen or lower alkyl;
- $R^{17}$ is hydrogen, lower alkyl or a sugar derivative;
- $R^{19}$ and $R^{20}$, which may be the same or different, are hydrogen or lower alkyl, or where p is 1, may with the cyclic ring to which $CR^{19}R^{20}$ is attached form a fused ring system;
- $R^{21}$ is hydrogen, alkyl, aralkyl or aryl;
- $E^1$ is a monodentate neutral ligand;
- $G^1$ is nitrogen, 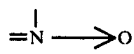

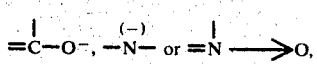

$J^1$ is a chain of 3 or 4 atoms consisting either exclusively of carbon atoms or carbon atoms together with one or more hetero atoms which may be the same or different, which chain with the group —C----G¹— forms an aromatic system, $L^1$, each of which may be the same or different, represents a substituent attached to a carbon atom in the chain $J^1$ and is hydrogen, alkyl, aralkyl, aryl or a substituent containing a hetero-atom, or two groups $L^1$ together with the ring to which they are attached form a fused ring system;

M is a metal from the first or second series of the main group of transition metals;

r is 0 or 1;

q is 0, 1 or 2 provided that q+r are 1, 2 or 3;

p is 0, 1 or 2 and s is the number of carbon atoms in the chain $J^1$.

5. A process as claimed in claim 4 characterised in that in the general formulae for the catalysts, r is 0, q is 1, $R^{14}$ and $R^{16}$ are hydrogen, $R^{15}$ is $CH_2OR^{22}$ in which $R^{22}$ has the meaning defined in claim 4, $R^{17}$ is lower alkyl, $L^1$ is hydrogen and $J^1$ is

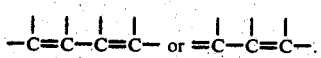

6. A process as claimed in claim 4 characterised in that in the general formulae for the catalysts p is 0, $R^{21}$ is hydrogen, $J^1$ is

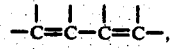

$L^1$ is hydrogen, s is 4 and $G^1$ is nitrogen or

7. A process as claimed in claim 1 characterised in that the catalysts of class (v) have one of the general formulae:

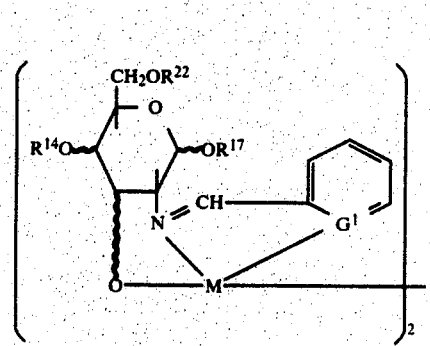

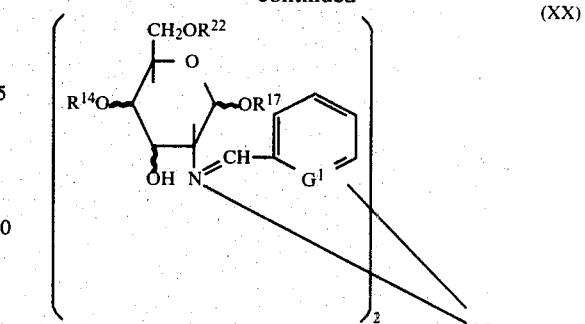

wherein $R^{17}$ is lower alkyl, $R^{14}$ and $R^{22}$ are hydrogen, or together form a divalent hydrocarbon radical, $G^1$ is nitrogen or

and $E^1$ is a monodentate neutral ligand.

8. A process as claimed in claim 1 characterised in that, in catalysts of class (vi) derived from compounds of the general formula (VA) containing groups $J^2$ and $K^2$ represented by formula (VB), $R^{25}$, $R^{26}$, $R^{27}$ and $R^{30}$ are hydrogen, $R^{32}$ is substituted phenyl and n is 0.

9. A process as claimed in claim 1 characterised in that, in catalysts of class (vi) derived from compounds of the general formula (VA), $J^2$ and $K^2$ have the formula:

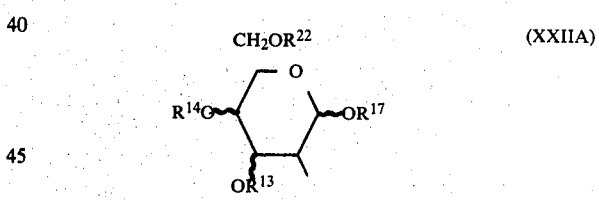

wherein $R^{17}$ is lower alkyl, $R^{13}$ is hydrogen and $R^{14}$ and $R^{22}$ are both hydrogen or together form a divalent hydrocarbon group.

10. A process as claimed in claim 1 characterised in that the catalysts of class (vi) have the general formula:

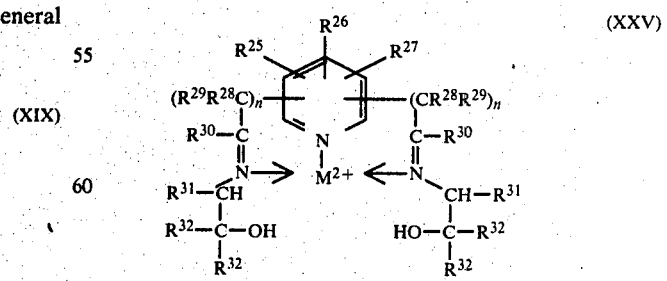

wherein $R^{25}$, $R^{26}$, $R^{27}$, $R^{28}$, $R^{29}$, $R^{30}$, $R^{31}$, $R^{32}$ and n have the meanings defined in claim 1, and M is a metal from the first or second series of the main group of transition metals.

* * * * *